US00PP16596P2

(12) United States Plant Patent
Gaalen

(10) Patent No.: US PP16,596 P2
(45) Date of Patent: May 30, 2006

(54) ***PHLOX* PLANT NAMED 'PLEASANT FEELINGS'**

(50) Latin Name: *Phlox paniculata*
Varietal Denomination: Pleasant Feelings

(76) Inventor: Irenaeus Anthounius Maria van Gaalen, Sionsweg 26, 2286 KL, Rijswijk (NL)

( * ) Notice: Subject to any disclaimer, the term of this patent is extended or adjusted under 35 U.S.C. 154(b) by 113 days.

(21) Appl. No.: 10/959,837

(22) Filed: Oct. 6, 2004

(51) Int. Cl.
*A01H 5/00* (2006.01)

(52) U.S. Cl. ..... Plt./320
(58) Field of Classification Search ..... Plt./320
See application file for complete search history.

(56) References Cited

PUBLICATIONS http;//www.rvg.nl/plants_all.htm, Jul. 11, 2003.*
http://www.rvg.nl/, Jul. 11, 2003.*
UPOV–Rom, Plant Variety Database 2005/01, GTI Jouve Retrieval Software, hit on 'Pleasant Feelings'.*

* cited by examiner

*Primary Examiner*—Anne Marie Grunberg
(74) *Attorney, Agent, or Firm*—Mark P. Bourgeois

(57) ABSTRACT

A new and distinct cultivar of *Phlox* plant named 'Pleasant Feelings' that is characterized by an upright habit, dark green leaves and flowers that consist of clusters of green bract like structures.

1 Drawing Sheet

Botanical classification: *Phlox paniculata.*
Variety denomination: 'Pleasant Feelings'.

BACKGROUND OF THE INVENTION

The present invention relates to a new and distinct cultivar of *Phlox* plant botanically known as *Phlox paniculata* and hereinafter referred to by the cultivar name 'Pleasant Feelings'.

In May of 2001, the new cultivar was discovered by the inventor, in a cultivated area of De Hoorn, The Netherlands. 'Pleasant Feelings' was discovered as a naturally occurring whole plant mutation within a population of *Phlox paniculata* 'Empty Feelings' (U.S. Plant Pat. No. 12,969).

'Pleasant Feelings' was first asexually propagated in May of 2001 in De Hoorn, The Netherlands by terminal cuttings. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Phlox* cultivar, 'Pleasant Feelings'. These traits in combination distinguish 'Pleasant Feelings' as a new and distinct cultivar apart from other known existing varieties of *Phlox.*

1. Phlox 'Pleasant Feelings' exhibits an upright habit.
2. Phlox 'Pleasant Feelings' exhibits dark green leaves.
3. Phlox 'Pleasant Feelings' does not have typical *Phlox* flowers with corollas, calyces and reproductive structures. The flowers of 'Pleasant Feelings' consist of clusters of green bract like structures.

The closest comparison variety is the parent plant *Phlox* 'Empty Feelings'. 'Pleasant Feelings' is different than 'Empty Feelings' in having green flowers. The flowers of 'Empty Feelings' are purple.

BRIEF DESCRIPTION OF THE DRAWING

The accompanying photograph illustrates the distinguishing traits of *Phlox* 'Pleasant Feelings'. The plant in the photograph shows an overall view of a 2 year old plant. The photograph was taken using conventional techniques and although colors may appear different from actual colors due to light reflectance it is as accurate as possible by conventional photographic techiques.

BOTANICAL DESCRIPTION OF THE PLANT

The following is a detailed description of the new *Phlox* cultivar named 'Pleasant Feelings'. Data was collected in Rijswijk, The Netherlands from 2 year old field grown plants. The time of year was Summer and the daytime temperature ranged from 18 to 32 degrees Centigrade. The temperature at night ranged from 10 to 18 degrees Centigrade. No photoperiodic treatments or growth retardants were used. Color determinations are in accordance with The Royal Horticultural Society Colour Chart 2001 edition, except where general color terms of ordinary dictionary significance are used. The growing requirements are similar to the species.

'Pleasant Feelings' has not been tested under all possible conditions and phenotypic differences may be observed with variations in environmental, climatic, and cultural conditions, however, without any variance in genotype.

Botanical classification: *Phlox paniculata.*
Annual or perennial: Perennial.
Parentage: 'Pleasant Feelings' is a naturally occurring whole plant mutation of *Phlox paniculata* 'Empty Feelings'.
Vigor: Moderate.

Growth rate: Approximately 15 cm. per month.
Growth habit: Upright.
Plant shape: Conical.
Plant height: Average 102 cm. in height.
Plant width: Average 42 cm. in width.
Suitable container size: 1.5 liter containers.
Propagation: Terminal cuttings.
Time to produce a rooted cutting or liner: Approximately 20–35 days.
Crop time: From a rooted cutting, approximately 30 weeks are required to produce a finished flowering plant.
High temperature tolerance: 30 degrees Centigrade.
Low temperature tolerance: USDA zone 6.
Root system: Fine and fibrous.
Number of harvestable stems per year: 4.
Cut flower longevity: 10 days.
Stem:
*Branching habit.*—Main shoots grow from base.
*Basal branching.*—No.
*Average number of lateral branches.*—4.
*Pinching.*—No.
*Lateral branch dimensions.*—84.5 cm. in length and 2 mm. in diameter.
*Lateral branch strength.*—Strong.
*Color.*—143A.
*Pubescence.*—Absent.
*Internode length.*—5.1 cm. between nodes.
*Shape.*—Round.
*Surface.*—Glabrous, slightly glossy.
Foliage:
*Texture.*—Both sides smooth.
*Leaf arrangement.*—Opposite.
*Compound or single.*—Single.
*Quantity of leaves per lateral branch.*—30.
*Leaf shape.*—Elliptic.
*Leaf apex.*—Acute.
*Leaf base.*—Attenuate.
*Leaf length.*—13.2 cm. in length.
*Leaf width.*—3.9 cm. in width.
*Pubescence.*—Absent.
*Leaf margin.*—Entire.
*Vein pattern.*—Pinnate.
*Young leaf color* (*upper surface*).—137A/139A.
*Young leaf color* (*lower surface*).—137C.
*Mature leaf color* (*upper surface*).—137A.
*Mature leaf color* (*lower surface*).—137C.
*Vein color* (*upper surface*).—143C/144A.
*Vein color* (*lower surface*).—143A.
*Leaf attachment.*—Petiolate.
*Petiole dimensions.*—1.5 mm. in length and 2.5 mm. in width.
*Petiole color.*—143C.
*Durability of foliage to stress.*—High.
Inflorescence:
*Inflorescence arrangement.*—Terminal panicle.
*Inflorescence type.*—Panicle.
*Inflorescence dimensions.*—17.5 cm in height and 18 cm in width.
*Flowering habit.*—Continuous.
*Quantity of flowers per inflorescence.*—Approximately 400.
*Quantity of buds per lateral stem.*—Approximately 400.
*Quantity of flowers and buds per plant.*—Approximately 1600.
*Flowering season.*—Summer.
*Time to flower.*—Approximately 12 weeks.
*Fragrance.*—None.
*Bud dimensions.*—4 mm. in length and 2 mm. in diameter.
*Bud shape.*—Ovate.
*Bud color.*—145A.
*Flower aspect.*—Upright and outward.
*Flower form.*—Flowers consist of clusters of bract like structures, the buds do not open, under each bud is a bract.
*Petaloids.*—No.
*Persistent or self cleaning.*—Persistent.
Sepals:
*Number of sepals.*—5.
*Sepal surface.*—Dull and glabrous.
*Sepal arrangement.*—Rotate.
*Sepal shape.*—Linear.
*Sepal margin.*—Entire.
*Sepal apex.*—Acute.
*Sepal base.*—Cuneate.
*Sepal dimensions.*—1.5 mm. in length and 0.75 mm. in width.
*Sepal color immature* (*upper side*).—145A.
*Sepal color immature* (*under side*).—145A.
*Sepal color mature* (*upper side*).—144A/B.
*Sepal color mature* (*under side*).—144A/B.
Calyx:
*Calyx shape.*—Rotate.
*Calyx dimensions.*—1.5 mm. in length and 2.0 mm. in diameter.
Peduncle:
*Peduncle dimensions.*—17.5 cm. in length and 2.0 mm. in diameter.
*Peduncle angle.*—Main peduncle 0 degrees, lateral peduncles 45 degrees.
*Peduncle color.*—143A.
*Peduncle strength*—Strong.
Pedicels: No.
Reproduction organs: None present.
Bracts:
*Bract arrangement.*—Under each bud is one bract.
*Bract length.*—5 mm.
*Bract shape.*—Linear.
*Bract tip.*—Acute.
*Bract base.*—Cuneate.
*Bract color immature.*—144A both sides.
*Bract color mature.*—137A both sides.
Seed: Seed production has not been observed.
Disease and pest resistance: Plants of the new *Phlox* have not been observed for disease or pest resistance.

It is claimed:

1. A new and distinct variety of *Phlox* plant named 'Pleasant Feelings' as described and illustrated.

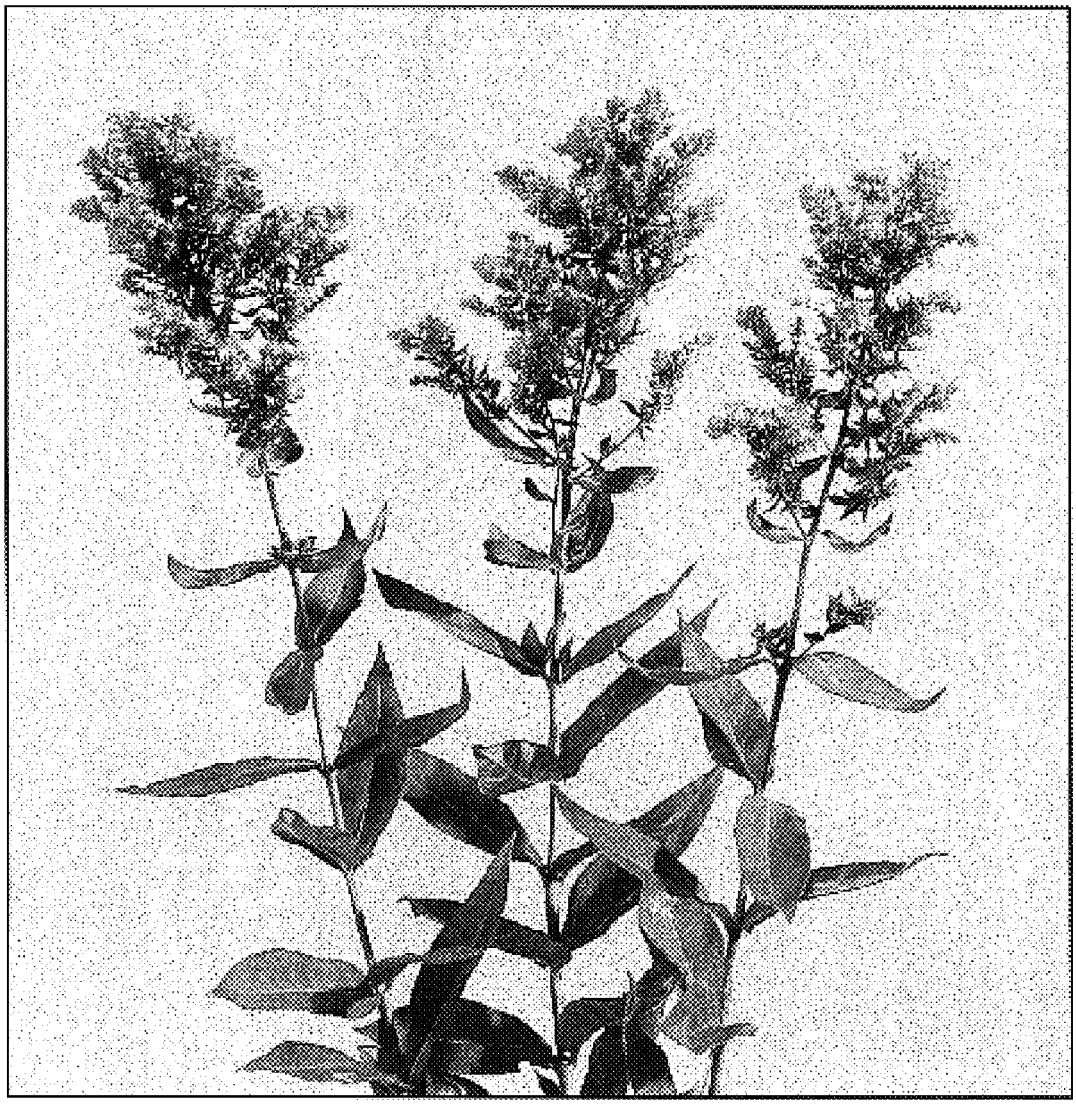

* * * * *